United States Patent
Hengerer

(10) Patent No.: US 7,565,273 B2
(45) Date of Patent: Jul. 21, 2009

(54) DETERMINATION OF THE AGE, IDENTIFICATION AND SEALING OF A PRODUCT CONTAINING VOLATILE COMPONENTS

(75) Inventor: Roland Hengerer, Juan les Pins (FR)

(73) Assignee: Accenture Global Services GmbH, Schaffhausen (CH)

( * ) Notice: Subject to any disclaimer, the term of this patent is extended or adjusted under 35 U.S.C. 154(b) by 682 days.

(21) Appl. No.: 10/766,738

(22) Filed: Jan. 27, 2004

(65) Prior Publication Data

US 2004/0186692 A1  Sep. 23, 2004

(30) Foreign Application Priority Data

Jan. 28, 2003 (EP) ................... 03354007

(51) Int. Cl.
*G06F 19/00* (2006.01)
*H03F 1/26* (2006.01)
*H04B 15/00* (2006.01)

(52) U.S. Cl. .......................... 702/189; 702/22; 702/30; 702/84; 73/23.34; 73/865.7; 422/83; 422/98; 435/287.1; 436/149; 116/214

(58) Field of Classification Search .............. 702/22, 702/30, 32, 81, 84, 104, 189; 73/23.34, 23–24, 73/34, 865.7; 422/88, 83, 98; 435/287.1; 436/149; 116/214
See application file for complete search history.

(56) References Cited

U.S. PATENT DOCUMENTS

| | | | |
|---|---|---|---|
| 4,458,093 A | * | 7/1984 | Hall et al. .................... 568/378 |
| 5,118,936 A | * | 6/1992 | Purser ........................ 250/281 |
| 5,313,821 A | * | 5/1994 | Bett et al. ................... 73/23.34 |
| 5,474,937 A | * | 12/1995 | Anderson et al. ............. 436/27 |
| 5,508,515 A | * | 4/1996 | Enge .......................... 250/281 |
| 5,541,851 A | * | 7/1996 | Sato et al. ................... 700/266 |
| 5,811,152 A | * | 9/1998 | Cleary ........................... 427/8 |

(Continued)

FOREIGN PATENT DOCUMENTS

JP    06018516    1/1994

(Continued)

OTHER PUBLICATIONS

Kaneyasu et al., 'Smell Identification Using a Thick-Film Hybrid Gas Sensor', Jun. 1987, vol. CHMT-10, No. 2, pp. 267-273.*

(Continued)

*Primary Examiner*—Edward Raymond
*Assistant Examiner*—Elias Desta
(74) *Attorney, Agent, or Firm*—Brinks Hofer Gilson & Lione

(57) ABSTRACT

The invention concerns a method and system for determining the age of an object such as a product containing volatile components, comprising: measuring a first strength of a first scent with a first electronic sensor, the decay rate constant of the first scent being known; measuring simultaneously a second strength of a second scent with a second electronic sensor, the decay rate constant of the second scent being known; calculating a current scent ratio ($\sigma$) of the two scent strengths; and determining the age of the object from a reference time for which a reference scent ratio ($\sigma_0$) of the scent strengths has been registered.

13 Claims, 1 Drawing Sheet

U.S. PATENT DOCUMENTS

| | | | | |
|---|---|---|---|---|
| 6,327,576 | B1 * | 12/2001 | Ogasawara | 705/22 |
| 6,435,002 | B1 * | 8/2002 | Briggs | 73/23.2 |
| 6,598,459 | B1 * | 7/2003 | Fu | 73/23.34 |
| 6,631,333 | B1 * | 10/2003 | Lewis et al. | 702/24 |
| 6,689,438 | B2 * | 2/2004 | Kennedy et al. | 428/36.6 |
| 6,895,338 | B2 * | 5/2005 | Hsiung et al. | 702/22 |
| 7,087,552 | B2 * | 8/2006 | Blowers et al. | 504/114 |
| 2002/0142477 | A1 * | 10/2002 | Lewis et al. | 436/151 |
| 2004/0031314 | A1 * | 2/2004 | Flynn et al. | 73/40.7 |

FOREIGN PATENT DOCUMENTS

WO     WO 99/45514    *   9/1999

OTHER PUBLICATIONS

Gilbert et al., 'Individually recongnizable scent marks on flowers made by a solitary bee', 2001, IDE Publication, vol. 61, pp. 217-229.*

Blixt et al., 'Using an Electronic Nose for Determining the Spoilage of Vacuum-Packaged Food', 1999, IJOFM, vol. 46, pp. 123-134.*

Tominaga et al., Identification of New Volatile Thiols in the Aroma of Vitis Vinifera L. Var. Sauvignon Blac Wines, 1998, F&F Journal Publication, vol. 13, pp. 159-162.*

Kita, 'Attempts at Simplified Measurement of Odors in Japan Using Odor Sensors', Jan. 2001, SHIMADZU Publication, pp. 142-148.*

J. Hammond et al., "A semiconducting metal-oxide array for monitoring fish freshness", Sensors and Actuators, vol. 84, No. 2-3, May 15, 2002, pp. 113-122.

A. Legin et al., "Tasting of beverages using and electronic tongue", Sensors and Actuators, vol. 44, No. 1-3, Oct. 1, 1997, pp. 291-296.

P. M. Schweizer-Berberich et al., "Characterization of food freshness with sensor arrays", Sensors and Actuators, vol. 18, No. 1-3, Mar. 1, 1994, pp. 282-290.

Partial European Search Report completed on Jul. 18, 2003, for EP application No. 03354007.1 filed Jan. 28, 2003, 3 pgs.

Li, Jing, "The Cyranose Chemical Vapor Analyzer," Sensors, Aug. 2000 (also appears to have been available at http://www.sensorsmag.com/articles/0800/56/main.shtml as of Jun. 21, 2005), nine pages.

* cited by examiner

“DETERMINATION OF THE AGE, IDENTIFICATION AND SEALING OF A PRODUCT CONTAINING VOLATILE COMPONENTS”.

DETERMINATION OF THE AGE, IDENTIFICATION AND SEALING OF A PRODUCT CONTAINING VOLATILE COMPONENTS

CROSS-REFERENCE TO RELATED APPLICATIONS

This application claims priority benefit of European Patent Application Serial No. 03354007.1, filed Jan. 28, 2003, titled "DETERMINATION OF THE AGE, IDENTIFICATION AND SEALING OF A PRODUCT CONTAINING VOLATILE COMPONENTS".

FIELD OF THE INVENTION

The present invention relates to a method and system for determining the age of a product. More particularly, the present invention concerns a method and system to quantify the age of a product, which can be in the range between a few seconds and a few weeks or longer.

An example of application of the present invention is the "time stamping" of goods, i.e., indicating the time passed, for instance, since the packaging or opening of the product. For example, the invention may apply for monitoring the freshness of consumable goods by determining the "opened age" of a package containing goods with volatile components, for example, a bottle of milk or wine.

BACKGROUND OF THE INVENTION

Currently, the available systems for determining the freshness of goods (for example, using a color-changing ink for marking the product) are not quantitative. They typically only indicate if goods are fresh or old.

Further, systems using tags or stamps based on color-changing ink can usually not be located directly on consumable goods but only on packages (or in an envelope insulating the tag from the product) where it does not interfere with the product.

The present invention aims at providing a new solution for determining the age of goods or products.

Another purpose of the present invention is to provide an automatic system for determining the age of a product from a reference instant.

Another purpose of the present invention is to provide a system that is accurate over short time periods (days, hours, or even minutes).

Another purpose of the present invention is to provide a method and system for marking products, objects or goods with a volatile identification code.

Another purpose of the present invention is to provide a method and system to seal a package by filling it with a scent that leaks out if the package is opened.

BRIEF SUMMARY OF THE INVENTION

To attain these purposes and others, the present invention uses chemical sensors called "electronic noses" to acquire digital descriptions of the scent of the product whose age is to be determined.

An electronic nose comprises at least one sensor and returns a number (measurement) for each sensor. Conventionally, a well-defined set of measurements produced for a given product constitutes the smell print (or signature) of that product. This smell print can be based either on inherent ingredients or on added scent markers with known scent signal characteristics.

The invention takes benefit of the fact that the smell signature of goods containing suitable volatile components decays (in intensity) with time. More particularly, for consumable products, the decay depends on the time from which the products are in contact with air or are no longer confined (in a package for instance). However, a problem is that the age of a product cannot be determined directly from the scent strength measured with an "electronic nose." Indeed, the measured signal does not only depend on time but also on other external parameters (comprising, among others, temperature, distance between the sensor and the object, atmospheric pressure) for which the time variation is unknown.

To solve this difficulty, the invention measures at least two scent prints of the product under the same external conditions. Then, by forming the ratio of the two measured values, the contribution of external parameters can be eliminated.

According to the present invention, the age determination is made with respect to a reference time. For example, for determining the opened age of a bottle of wine or a package containing goods, the reference scent print corresponds to a scent print measured at the instant the bottle or package was opened. According to another embodiment, in the case of products that do not interfere with the scents used for age determination purposes as long as the package is closed, the reference scent is determined at the instant of packaging in a tight envelope.

It should be noted that the invention is not limited to "smelling" scents, i.e., to smells detectable by the human nose. Indeed, electronic noses can also detect "non-smelling" scents.

According to an exemplary embodiment, a large number (about ten) of sensors of an electronic nose are used not only to establish the age of a product but also to identity the product. Indeed, smell prints of products can also be used for identification purposes, as each product, goods or object with volatile components has a unique scent print.

According to yet another exemplary embodiment, the scent print used for age determination purposes corresponds to a scent sprayed on the surface of the product at an initial time. Hence, the invention applies to products that do or do not have their own scents. According to this embodiment, the reference scent print can be preregistered. The sprayed scent preferably corresponds to a non-smelling scent. Hence, the object is marked with an "invisible" scent print.

BRIEF DESCRIPTION OF THE DRAWINGS

The foregoing and other purposes, features, aspects and advantages of the invention will become apparent from the following detailed description of embodiments, given by way of illustration, and not limitation, with reference to the accompanying drawings, among which.

Figure 1:
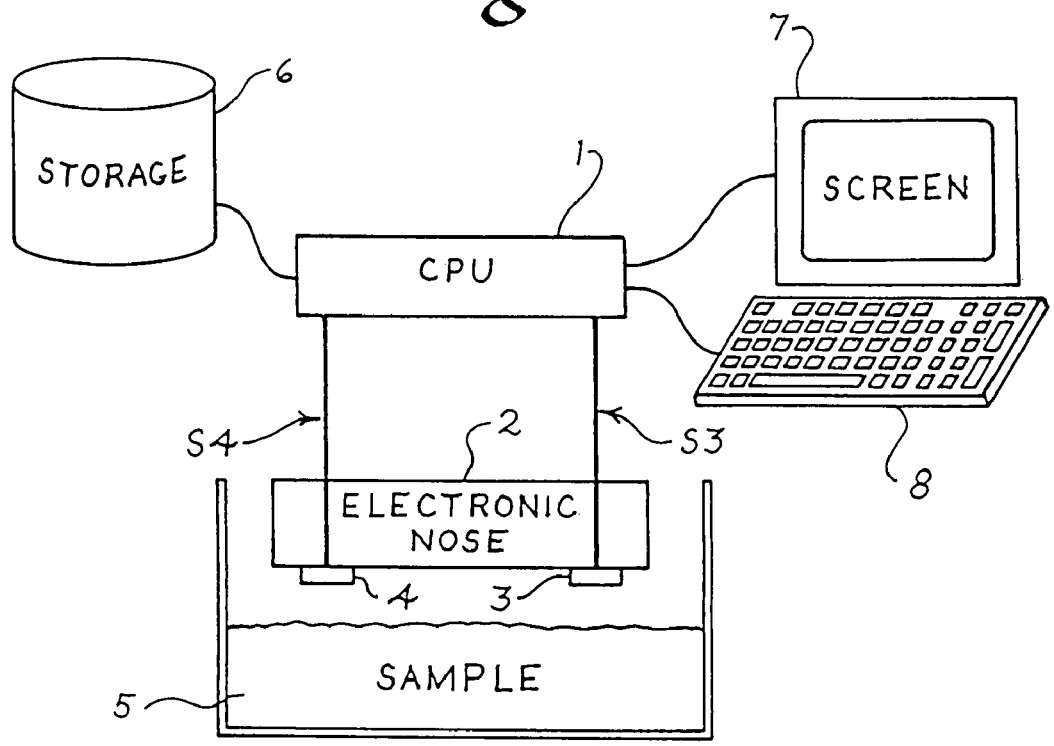
FIG. 1 schematically represents a system according to an embodiment of the present invention.

For clarity, only the elements and steps useful to the understanding of the invention have been shown in the drawings and will be disclosed hereafter. Specifically, the programming steps relating to the system of the invention will not be detailed, as they will readily occur to those skilled in the art. Further, the invention will be disclosed in connection with a specific embodiment applied to single volatile component scents. However, the invention applies more generally to any composite scent (with a similar time dependence on the signature).

DETAILED DESCRIPTION OF THE INVENTION

Due to physical evaporation (and/or chemical decomposition) of a scent, the scent intensity of a given (single or composite) scent follows this (experimentally confirmed) formula in close approximation:

$$I(t,\xi(t)) = I_0 \eta(\xi(t)) \cdot e^{-\alpha t}, \quad (1)$$

where t designates time, I designates a measure for the scent strength measured quantitatively with a sensor of a known electronic nose, $\alpha$ designates a decay rate constant depending on the volatile component(s) of a scent, and $\eta$ designates an unknown function taking into account all external parameters $\xi$ such as temperature, atmospheric pressure, distance to the object, etc., for which the evolution versus time is not necessarily known.

Due to the unknown function $\eta(\xi(t))$, it is not possible to solve directly the above formula, even knowing the measured value $I_0$ at a reference instant.

According to the invention, the scent signals are measured for at least two different scents (two different sensors of the electronic nose with different decay constants ($\alpha$). Consequently, the above formula applied to both scent signals can be expressed in the following manner, where indexes 1 and 2 designate the respective scents or sensors:

$$I_1(t,\xi(t)) = \eta(\xi(t)) I_{01} \cdot e^{-\alpha_1 t}, \text{ and}$$

$$I_2(t,\xi(t)) = \eta(\xi(t)) I_{02} \cdot e^{-\alpha_2 t}.$$

Since the two signals are always measured simultaneously, the term $\eta(\xi(t))$ is essentially identical in both expressions. This constitutes a close approximation provided that the two substances show similar absorption behavior (e.g., due to identical attachment groups of the molecules) and that the external parameters are kept within reasonable limits (e.g. ±20%).

The ratio $\sigma$ of the two measurement signals depends only on the time and on decay constants given by each sensor:

$$\sigma = \frac{I_2(t,\xi(t))}{I_1(t,\xi(t))} = \sigma_0 \cdot e^{(\alpha_1 - \alpha_2)t}, \quad (2)$$

where $\sigma_0$ designates a measured reference ratio at a reference time (for example, at the opening of a bottle or at the packaging of goods). The ratio $\sigma_0$ is measured at a reference time that defines the age zero of the product. The ratio $\sigma_0$ is stored in the system for age determination purposes. Alternatively, the ratio $\sigma_0$ is preregistered in the system for several age determinations based on the same reference time. So, knowing the reference ratio $\sigma_0$ and the decay constants $\alpha_1$ and $\alpha_2$, the age t of the product from a reference instant is determined by equation (3):

$$t = (\alpha_1 - \alpha_2)^{-1} \cdot \ln\left(\frac{\sigma}{\sigma_0}\right). \quad (3)$$

In the above formula, absolute values are considered. The scent volatility which conditions the decay rate of a substance can be adjusted to the requirements (targeted time span, etc.) by selecting the appropriate substances for which the scents are measured.

The decay rate constants $\alpha_1$ and $\alpha_2$ can be determined, for example during a learning step or a characterization step of the system, by measuring the scent intensity versus time of the corresponding volatile components when recorded with the sensors of the system. Decay rate constants $\alpha_1$ and $\alpha_2$ are related to the half time $\tau_{1/2}$ of the used scents, i.e., the duration in which the respective signal strengths of the corresponding sensors are divided by two, by the following formula:

$$\alpha = \frac{\ln(2)}{\tau_{\frac{1}{2}}}$$

According to another embodiment of the invention, it is possible to affect a volatile product identification code to a product only by spraying m(m=2, 3, 4, . . . ) scents (or a composite scent containing m volatile components) on it. Given the large number n (n>1000) of existing smells, there are $$\binom{n}{m} = \frac{n!}{(n-m)! m!}$$

possible combinations (e.g. for n=500 and m=4 more than 2 billion). This simple product identification code can also be hidden by using non-smelling agents.

FIG. 1 schematically illustrates a system according to an embodiment of the present invention. Such a system comprises a central processing unit 1 receiving measurement signals S3 and S4 from an electronic nose 2. Sensors 3 and 4 of the electronic nose are disposed above a sample 5 to be analysed.

Electronic noses are known devices based on an array of chemical sensors. Each sensor in the sensor array responds specifically to a given chemical compound. In that way, it is possible to obtain a "smell print" for a given chemical compound or mixture. Conventionally, this signature or print is a set of digital readings or measurements corresponding to the reading from the set of sensors. The number of sensors is usually comprised between 10 and 100, for example 32 or 64 depending on the desired accuracy of the identification.

According to the present invention, only two sensors 3 and 4 are used for age determination. However, other sensors may still be used if the age determination is combined with an identification based on the scent of the product.

According to an exemplary embodiment of the invention, an electronic nose known under the commercial name "Cyranose 320", with 32 sensors, is used to obtain a set of scent prints. According to this exemplary embodiment, each sensor measurement is a decimal value with seven significant figures.

Preferably, the system further comprises local or remote storage peripheral(s) 6 for containing the parameters of the system (and if required, the identification references of the object to be processed), a screen 7, a keyboard 8 and any other input-output peripherals adapted to the application. For example, the electronic nose 2 is an acquisition peripheral of a computer performing the method according to the invention.

Alternatively, if the system is dedicated to a limited test (for example, the freshness of a product), its components (two sensors, the interpretation unit, the processing unit, etc.) can be integrated in a portable device with simplified indicators (green and red LEDs or a simplified display of the age) for the results. If necessary, the portable device can be equipped with a measuring chamber containing the sensors in order to shield the sensors from external influences. This measuring chamber can be realized, e.g., by an open cube with the open face (or an aperture) directed toward the object.

Figure 2:
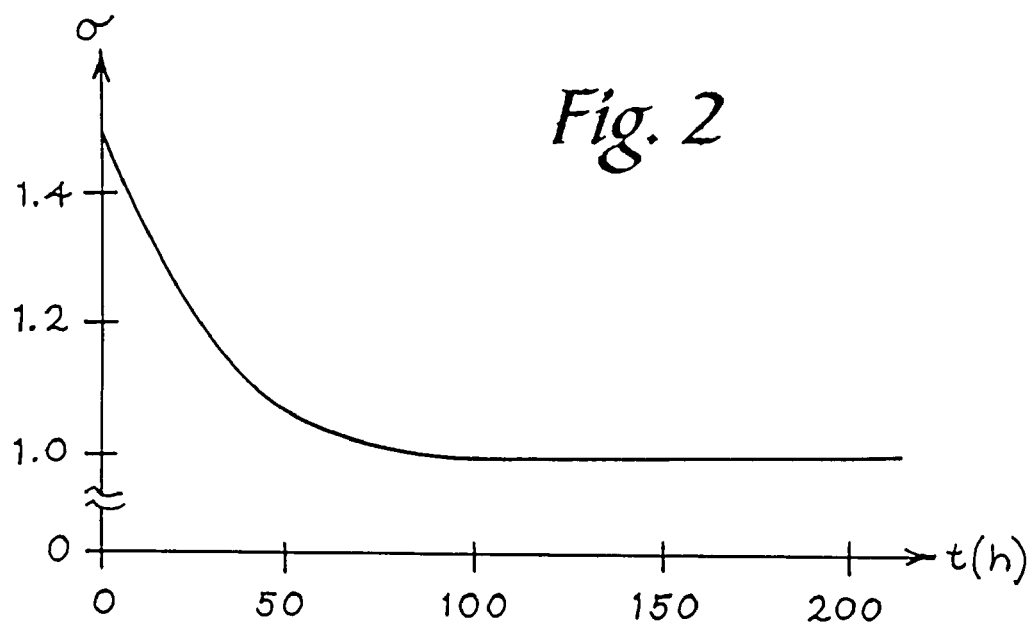
FIG. 2 schematically illustrates the time response of the interpreted scent signal of a pair of scents according to an embodiment of the present invention.

FIG. 2 (interpolation of experimental results) schematically illustrates the ratio $\sigma$ of the signal intensity of two sensors (3, 4, FIG. 1) of an electronic nose with respect to time. The reference ratio $\sigma$ corresponds to the initial value of ratio $\sigma_0$ at time 0. In this example, it can be seen that the age of a sample containing the corresponding two scent components (two commercial perfumes) can be measured up to about 100 hours, thereafter the signal strengths are no longer interpretable.

After having calculated and stored the reference ratio $\sigma_0$ (on the basis of initial measurements), the measurement of any current ratio $\sigma$ of the scent data (signal strength of the two sensors) provides, through formula (3), the age of the product from the reference instant.

According to a simplified embodiment (for example, in the case of a simplified device responsive to only two scents), the curve can be registered and the age determination directly obtained by comparing the current value to the curve.

However, in a preferred embodiment, the age is calculated by applying formula (3) to the measured ratio. This renders the system more versatile. Indeed, the same formula can be used for measuring ages on the basis of different pairs of scents. It is sufficient to change the two decay rate constants $\alpha_1$ and $\alpha_2$ (which are, in practice, registered numbers) with respect to the pairs of scents to which the system is responsive. The initial reference ratio $\sigma_0$ is then preferably registered during a time initialization step by the user.

The selection of the scents to be measured for age determination depends on the kind of product.

It should be noted that, even for a freshness measurement, the measured scents are not necessarily part of the product itself. It is also possible to mark the product at the time of packaging (for example, inside the package) or at the time of opening by spraying the two scents on it.

An advantage of the present invention is that it makes it possible to determine quantitatively the age of a product over periods of short duration.

Another advantage of the invention is that its implementation does not require visible marks on the products.

Another advantage of the invention is that the age determination can be combined with an identification of the product or possible contamination.

Another advantage of the invention is that the age determination can be combined with the time-dependent marking of a product (e.g., during the manufacturing cycle) or person (e.g., at the entrance of a building or at an airport gate for security reasons).

Another advantage of the invention is that it can be used for the sealing of a product. The sealing is achieved by introducing into an impermeable seal, attached to or containing the object, at least two volatile components, said components being chosen for containing the respective first and second scents to which the system is responsive. The reference ratio $\sigma_0$ corresponds to the scent strengths ratio when sealing. If the seal has been broken some of the volatile components will have leaked out so that a current scent ratio $\sigma$ should differ substantially (by more than an acceptable error $\epsilon$, i.e., $|\sigma-\sigma_0|>\epsilon$) from the provided value for an intact seal which should be close to the initial value at instant zero (reference scent ratio $\sigma_0$).

The practical implementation of the invention using known tools (scent sensors, computerized devices) is within the ability of someone with ordinary skills in the art.

Having thus described at least one illustrative embodiment of the invention, various alterations, modifications and improvements will readily occur to those skilled in the art. Such alterations, modifications, and improvements are intended to be within the spirit and scope of the invention. Accordingly, the foregoing description is by way of example only and is not intended to be limiting. The invention is limited only as defined in the following claims and the equivalent thereto.

The invention claimed is:

1. A method for determining an age of an object comprising:
    measuring a first strength of a first scent of said object with a first electronic sensor, a decay rate constant ($\alpha_1$) of said first scent being known;
    measuring simultaneously a second strength of a second scent of said object with a second electronic sensor, a decay rate constant ($\alpha_2$) of said second scent being known;
    calculating a current scent ratio ($\sigma$) of said first and second scent strengths;
    calculating said age of said object starting from a reference time for which a reference scent ratio ($\sigma_0$) of said scent strengths has been registered; and
    displaying said age.

2. The method of claim 1, wherein said calculating said age is performed by applying to said current scent ratio $\sigma$ the following formula, giving said age of said object as represented by the symbol t:

$$t = (\alpha_1 - \alpha_2)^{-1} \cdot \ln\left(\frac{\sigma}{\sigma_0}\right),$$

where $\sigma_0$ designates said reference scent ratio, and $\alpha_1$ and $\alpha_2$ designate said first and second decay rate constants of said first and second scents, respectively.

3. The method of claim 1, wherein said calculating said age is performed by comparing said current scent ratio ($\sigma$) to preregistered data corresponding to respective age values.

4. The method of claim 1, wherein said reference scent ratio ($\sigma_0$) is determined by measuring said first and second scent strengths at an initial time from which said age of said object is to be determined.

5. The method of claim 1, wherein said first and second decay rate constants ($\alpha_1$, $\alpha_2$) are determined during a process of characterizing of sensors measuring said first and second scents.

6. The method of claim 1, wherein said first scent is included in a first volatile compound sprayed on said object and said second scent is included in a second volatile compound sprayed on said object.

7. The method of claim 6, wherein said reference scent ratio ($\sigma_0$) is preregistered and corresponds to said first and second scent strengths when spraying said compound.

8. A method of determining a freshness of goods from a reference time, comprising:
    measuring a first strength of a first scent of said goods with a first electronic sensor, a decay rate constant ($\alpha_1$) of said first scent being known;

measuring simultaneously a second strength of a second scent of said goods with a second electronic sensor, a decay rate constant ($\alpha_2$) of said second scent being known;

calculating a current scent ratio ($\sigma$) of said first and second scent strengths;

calculating said freshness of said goods starting from a reference time for which a reference scent ratio ($\sigma_0$) of said scent strengths has been registered; and displaying an indicator of said freshness.

9. A method of sealing an object, comprising:

introducing into an impermeable seal attached to said object a first volatile component;

introducing into said impermeable seal a second volatile component;

simultaneously determining a first scent strength of said first volatile component and a second scent strength of said second volatile component at a time when said impermeable seal is unbroken;

determining a reference scent ratio ($\sigma_0$) from said first scent strength and said second scent strength; and determining whether said impermeable seal is broken based on said reference scent ratio ($\sigma_0$).

10. The method of claim 9, further comprising:

simultaneously determining a first scent strength of said first volatile component and a second scent strength of said second volatile component at a second time that is subsequent to said time when said impermeable seal is unbroken; and calculating a current scent ratio ($\sigma$) from said first scent strength and said second scent strength that are determined at said second time, wherein said seal is considered to have been broken if said current scent ratio ($\sigma$) differs from said reference scent ratio ($\sigma$) by more than an acceptable error $\epsilon$.

11. A system for determining an age of an object containing first volatile component and a second volatile component, comprising:

a first electronic sensor that generates a first signal in response to a first scent of said first volatile component;

a second electronic sensor that generates a second signal in response to a second scent of said second volatile component;

a calculating unit for calculating a current scent ratio ($\sigma$) based on said first and second signals, and for extracting said age of said object from a reference time for which a reference scent ratio ($\sigma_0$) is registered; and a display for displaying an indicator of said age.

12. A method of marking an object with a volatile identification code, comprising:

spraying a first volatile component onto said object;

spraying a second volatile component onto said object, wherein volatile characteristics of said first and second volatile components sprayed on said object define said volatile identification code; and sensing said volatile characteristics via a set of sensors that generate a distinctive signature that are associated with spraying both said first volatile component and said second volatile component on said object.

13. The system of claim 11, wherein said calculating unit extracts said age of said object by applying to said current scent ratio $\sigma$ the following formula, giving said age of said object as represented by the symbol t:

$$t = (\alpha_1 - \alpha_2)^{-1} \cdot \ln\left(\frac{\sigma}{\sigma_0}\right),$$

where $\sigma_0$ designates said reference scent ratio, and $\alpha_1$ and $\alpha_2$ designate first and second decay rate constants of said first and second scents, respectively.

* * * * *

UNITED STATES PATENT AND TRADEMARK OFFICE
CERTIFICATE OF CORRECTION

| | | |
|---|---|---|
| PATENT NO. | : 7,565,273 B2 | Page 1 of 1 |
| APPLICATION NO. | : 10/766738 | |
| DATED | : July 21, 2009 | |
| INVENTOR(S) | : Hengerer | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 755 days.

Signed and Sealed this
Fifth Day of February, 2013

Teresa Stanek Rea
*Acting Director of the United States Patent and Trademark Office*